(12) United States Patent
Sharma et al.

(10) Patent No.: US 6,633,833 B2
(45) Date of Patent: Oct. 14, 2003

(54) METHOD AND APPARATUS FOR REMOTE DIAGNOSIS OF AN ULTRASOUND SCANNER

(75) Inventors: Sanjeev Sharma, Waukesha, WI (US); Stephen Peshman, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 12 days.

(21) Appl. No.: 09/683,327

(22) Filed: Dec. 14, 2001

(65) Prior Publication Data

US 2003/0115018 A1 Jun. 19, 2003

(51) Int. Cl.[7] ................................................ G06F 11/00
(52) U.S. Cl. ..................... 702/188; 600/437; 128/904
(58) Field of Search ................. 128/904; 73/1.82–1.86; 702/39, 182–188; 600/437

(56) References Cited

U.S. PATENT DOCUMENTS

| | | |
|---|---|---|
| 5,715,823 A | 2/1998 | Wood et al. |
| 5,851,186 A | 12/1998 | Wood et al. |
| 5,891,035 A | 4/1999 | Wood et al. |
| 6,224,551 B1 | 5/2001 | Mullen |
| 6,272,469 B1 | 8/2001 | Koritzinsky |

*Primary Examiner*—Marc S. Hoff
*Assistant Examiner*—Andrew P Morris
(74) *Attorney, Agent, or Firm*—McAndrews, Held & Malloy, Ltd.; Peter J. Vogel; Michael A. Dellapenna (57) ABSTRACT

A method and apparatus are disclosed for diagnosing multiple ultrasound scanners from a remote location by applying a diagnostic middleware architecture to act as an interface between a web server and diagnostics section within the scanners. A computer that is remote to the scanners interfaces to the web servers of the scanners over a network. The remote computer has a web browser to survey the scanners by communicating with the web servers over the network. The diagnostic middleware architecture initiates execution of diagnostic programs within the scanners in response to client requests received by the web servers from the remote computer over the network. Diagnostic results are generated within the scanners when running the diagnostic programs of the scanners. Log files are generated within the scanners during normal operation of the scanners. The diagnostic middleware architecture reads the diagnostic results and log files and translates the information such that the web servers are able to transfer the information to the remote computer over the network. The information is displayed to an operator by the remote computer.

62 Claims, 2 Drawing Sheets

METHOD AND APPARATUS FOR REMOTE DIAGNOSIS OF AN ULTRASOUND SCANNER

BACKGROUND OF INVENTION

Certain embodiments of the present invention relate to a medical diagnostic ultrasound scanner. More particularly, certain embodiments relate to a method and apparatus for diagnosing an ultrasound scanner from a remote location using platform/server independent programs.

Ultrasound scanners to detect faults, problems, and general status within the scanner are well established. Ultrasound scanners typically comprise different hardware and software implementations that perform various operations such as scan data collection and scan data conversion. There are different software diagnostic tests that perform routine troubleshooting of the hardware assemblies. Other tests provide data on software functioning and general scanner status by logging the data in files.

The diagnostic software tests are resident on the scanner and may be operated by a person having direct access to the console of the scanner. However, the tests are not always accessible remotely, that is, from a remote computer through a connection to, for example, a network through a modem.

Other scanners provide remote access through, for example, a VT-100 based remote interface or a common gateway interface (CGI) used for performing various remote services. The interfaces are dependent on specific software and hardware configurations and are not always optimized in terms of performance as the software platform is changed or upgraded. To improve the performance, a new interface that is consistent with the latest software platform would have to be designed.

For example, a method described in U.S. Pat. No. 5,715,823 to Wood et al. describes using common gateway interface (CGI) programs to access ultrasound images and diagnostic data. A method described in U.S. Pat. No. 5,891,035 to Wood et al. describes accessing images and information from internal and external databases by means of a browser within an ultrasound system and connecting the browser to a network. A method described in U.S. Pat. No. 5,851,186 to Wood et al. describes electronically acquiring a diagnostic ultrasound image over a communications network such that an ultrasound system has a server. A method described in U.S. Pat. No. 6,224,551 B1 to Mullen describes storing ultrasound image data in a database storage device and using an internet protocol. A method described in U.S. Pat. No. 6,272,469 B1 to Koritzinksy et al. describes downloading operational protocols to diagnostic machines from a remote location over a network.

The well-established Internet enables computers at one location to communicate with computers at other locations. The technique of packet switching is typically used to transfer data from one computer to another over the Internet. Information from one user of a network is sent to another user of the network by breaking the information up into discrete units of digital information called packets. Packets of information are transferred across the network by high-speed routers that seek out a network route from one point to another in the network. At a destination point in the network, packets are received and reassembled to re-institute the originally sent message of information.

Transferring information via packets allows a network to accommodate many messages at a time by interleaving packets originating from different locations. Many computers may operate on a network at the same time and may transfer information quickly across the network in the form of packets. The higher cost of a dedicated communication path is avoided. However, as the number of users of the network increase, the larger number of messages being sent may result in a longer amount of time being required to transfer all of the packets in any given message over the network to its destination. But enhancements in computer technology and performance over time allow higher volumes of information to be transferred across a network at faster rates.

The Internet comprises multiple networks that allows for the transfer of information among many users who are linked into the network. To facilitate the transfer of information across the Internet, the World Wide Web (WWW) was created to be used as a high-level user interface to the Internet. A distributed menu system is provided by the WWw where menu pages are displayed such that a user may request information from another system on the Internet. The WWW provides the ability for a user to hop from one web site of information to another by way of displayed hypertext links. A hypertext link allows a user to click on a hypertext component, transferring to a web page associated with that hypertext component, regardless of where the web page is actually located or hosted. A user may download information from the web page and/or go on to another or previous web page in a similar manner. By employing hypertext linking, a user may rapidly link to the desired information on the WWW for which he is searching. Information received from a given web site may be formatted as text, images, graphics, video, and audio.

By incorporating a standard server into an ultrasound machine, the power of the Internet may be employed to access diagnostic data generated by the ultrasound scanner. However, the interface between the server and diagnostics section within the scanner has previously been customized for the scanner and server.

A need exists to be able to activate performance of diagnostic functions on scanners from a remotely located computer and display certain results of the diagnostic functions on the remotely located computer such that the diagnostics interface is platform/server independent and may be used on multi-generational products.

SUMMARY OF INVENTION

An embodiment of the present invention provides for diagnosing multiple ultrasound scanners, being of differing platform types, from a remote location by applying a diagnostic middleware architecture acting as an interface between a diagnostics section of the scanners and a web server within the scanners. The diagnostic middleware architecture is platform/server independent and may be used on multi-generational products. As used herein, platform/server-independent means independent of the operating system and hardware on which the programs of the diagnostic middleware architecture are being run. The ultrasound scanners are surveyed from a remote location over a network by communicating with the servers over the network. The diagnostic middleware architecture initiates execution of diagnostic programs within the scanners in response to client requests received by the servers from the remote location. The diagnostic programs generate diagnostic results. Log files are generated within the scanners during normal operation of the scanners. The diagnostic middleware architecture translates the diagnostic results and log files to the web servers and the web servers transfer the information to the remote location over the network. The information is displayed to an operator at the remote location.

Apparatus is provided for diagnosing multiple ultrasound scanners, being of differing platform types, from a remote location by employing a diagnostic middleware architecture acting as an interface between a diagnostic programs module within the scanners and a web server within the scanners. The diagnostic middleware architecture is platform/server independent and may be used on multi-generational products. A computer that is remote to the scanners interfaces to the web servers of the scanners over a network. The remote computer has a web browser to survey the scanners by communicating with the web servers within the scanners over the network. The diagnostic middleware architecture initiates execution of diagnostic programs within the diagnostic programs modules of the scanners in response to client requests received by the web servers from the remote computer over the network. The diagnostic programs generate diagnostic results. Log files are generated within the scanners during normal operation of the scanners. The diagnostic middleware architecture translates the diagnostic results and log files to the web servers and the web servers transfer the information to the remote computer over the network. The information is displayed to an operator by the remote computer.

A method is also provided for diagnosing multiple ultrasound scanners, being of differing platform types, from a remote location by applying a diagnostic middleware architecture acting as an interface between diagnostic programs within the scanners and a web server within the scanners. The diagnostic middleware architecture is platform/server independent and may be used on multi-generational products. The web servers of the scanners interface to a remote location. The scanners are surveyed from the remote location by communicating with the web servers within the scanners. The diagnostic middleware architecture initiates execution of diagnostic programs within the scanners in response to client requests received by the web servers from the remote location. The diagnostic programs generate diagnostic results. Log files are generated within the scanners during normal operation of the scanners. The diagnostic middleware architecture translates the diagnostic results and log files to the web servers and the web servers transfer information to the remote location. The information is displayed to an operator at the remote location.

Certain embodiments of the present invention afford an approach to activate diagnostic functions on ultrasound scanners of differing platform types from a remotely located computer, and display certain results of the functions on the remotely located computer such that the diagnostics interface is platform/server independent and may be used on multi-generational products.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION

Figure 1:
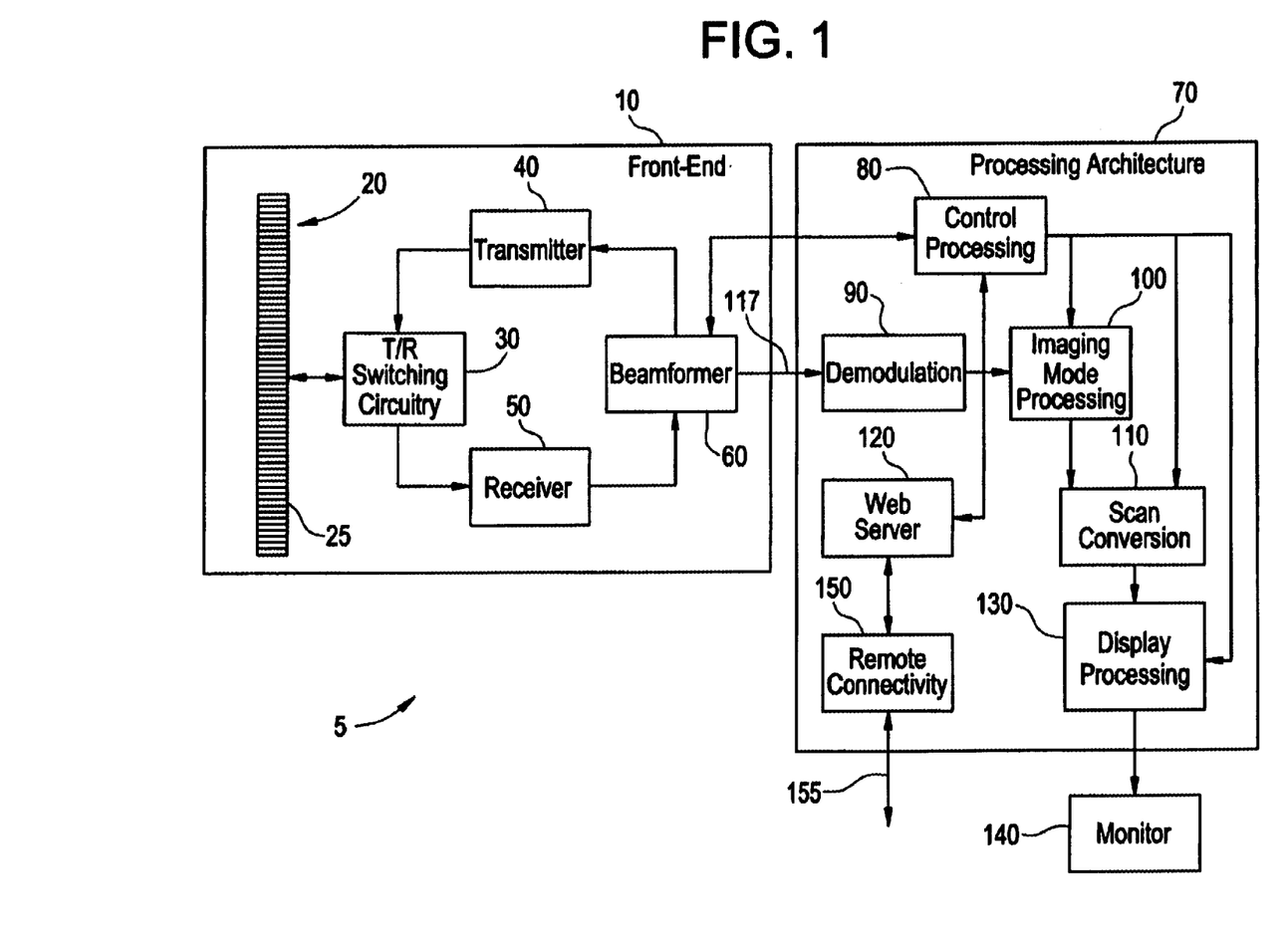
FIG. 1 is a schematic block diagram of a diagnostic ultrasound scanner formed in accordance with an embodiment of the present invention.

FIG. 1 is a schematic block diagram of an ultrasound system 5 in accordance with an embodiment of the present invention. The higher level illustrated elements of the ultrasound system 5 are the front-end 10 and the processing architecture 70. The front-end 10 comprises a transducer array 20 (comprising a plurality of transducer array elements 25), transmit/receive switching circuitry 30, a transmitter 40, a receiver 50, and a beamformer 60. Processing architecture 70 comprises a control processing module 80, a demodulation module 90, an imaging mode processing module 100, a scan conversion module 110, a display processing module 130, a web server 120, and a remote connectivity module 150. A monitor 140 is also provided.

The architectures and modules may be dedicated hardware elements such as circuit boards with digital signal processors or may be software running on a general purpose computer or processor such as a commercial, off-the-shelf PC. The various architectures and modules may be combined or separated according to various embodiments of the present invention.

In the front-end 10, the transducer array 20 is connected to the transmit/receive (T/R) switching circuitry 30. The T/R switching circuitry 30 is connected to the output of transmitter 40 and the input of receiver 50. The output of receiver 50 is input to beamformer 60. Beamformer 60 is further connected to the input of transmitter 40, to control processing module 80 and the input of demodulation module 90 in processing architecture 70 through digital interface 117.

In processing architecture 70, the output of demodulation module 90 is connected to an input of imaging mode processing module 100. Control processing module 80 interfaces to imaging mode processing module 100, scan conversion module 110, display processing module 130, and web server 120. An output of imaging mode processing module 100 is connected to an input of scan conversion module 110. An output of scan conversion module 110 is connected to an input of display processing module 130. Web server 120 is connected to remote connectivity module 150. The output of display processing module 130 is connected to the input of monitor 140. Remote connectivity module 150 provides the connection to an external network 250 (see FIG. 2) at connection 155.

The primary function of the ultrasound scanner 5 is to transmit ultrasound energy into a subject to be imaged, and receive and process backscattered ultrasound signals from the subject to create and display an image. To generate a transmitted beam of ultrasound energy, the control processing module 80 sends command data to the beamformer 60 which tells the beamformer to generate transmit parameters to create a beam of a certain shape that originates from a certain point at the surface of the transducer array 20 at a certain steering angle. The transmit parameters are sent from the beamformer 60 to the transmitter 40. The transmitter 40 uses the transmit parameters to properly encode transmit signals to be sent to the transducer array 20 through the T/R switching circuitry 30. The transmit signals are set at certain levels and phases with respect to each other and are provided to individual transducer elements 25 of the transducer array 20. The transmit signals excite the transducer elements 25 of the transducer array 20 to emit ultrasound waves with the same phase and level relationships. As a result, a transmitted beam of ultrasound energy is formed in a subject within a scan plane along a scan line when the transducer array 20 is acoustically coupled to the subject by using, for example, ultrasound gel. The process is known as electronic scanning.

The transducer array 20 is a two-way transducer, Once ultrasound waves are transmitted into a subject, the ultrasound waves are backscattered off of tissue and blood samples within the structure. The backscattered waves arrive at the transducer array 20 at different times, depending on the distance into the tissue they return from and the angle with respect to the surface of the transducer array 20 at which they return. The transducer elements 25 of the transducer array 20 are responsive to the backscattered waves and convert the ultrasound energy from the backscattered waves into received electrical signals.

The received electrical signals are routed through the T/R switching circuitry 30 to the receiver 50. The receiver 50 amplifies and digitizes the received signals and provides other functions such as gain compensation. The digitized received signals correspond to the backscattered waves received by each transducer element 25 at various times and preserve the amplitude and phase information of the backscattered waves.

The digitized received signals are sent to beamformer 60. The control processing module 80 sends command data to beamformer 60. Beamformer 60 uses the command data to form a receive beam originating from a point on the surface of transducer array 20 at a steering angle typically corresponding to the point and steering angle of the previous ultrasound beam transmitted along a scan line. The beamformer 60 operates on the appropriate received signals by performing time delaying and focusing, according to the instructions of the command data from the control processing module 80, to create received beam signals corresponding to sample volumes along a scan line in the scan plane within the subject. The phase, amplitude, and timing information of the received signals from the various transducer elements 25 is used to create the received beam signals.

The received beam signals are sent to processing architecture 70 over digital interface 117. Demodulation module 90 performs demodulation on the received beam signals to create pairs of I and Q demodulated data values corresponding to sample volumes within the scan plane. Demodulation is accomplished by comparing the phase and amplitude of the received beam signals to a reference frequency. The I and Q demodulated data values preserve the phase and amplitude information of the received signals.

The demodulated data is transferred to imaging mode processing module 100. Imaging mode processing module 100 uses parameter estimation techniques to generate imaging parameter values from the demodulated data in scan sequence format. The imaging parameters may comprise parameters corresponding to various possible imaging modes such as, for example, B-mode, color velocity mode, spectral Doppler mode, and tissue velocity imaging mode.

The imaging parameter values are passed to scan conversion module 110. Scan conversion module 110 processes the parameter data by performing a translation from scan sequence format to display format. The translation includes performing interpolation operations on the parameter data to create display pixel data in the display format.

The scan converted pixel data is sent to display processing module 130 to perform any final spatial or temporal filtering of the scan converted pixel data, to apply grayscale or color to the scan converted pixel data, and to convert the digital pixel data to analog data for display on monitor 140.

Figure 2:
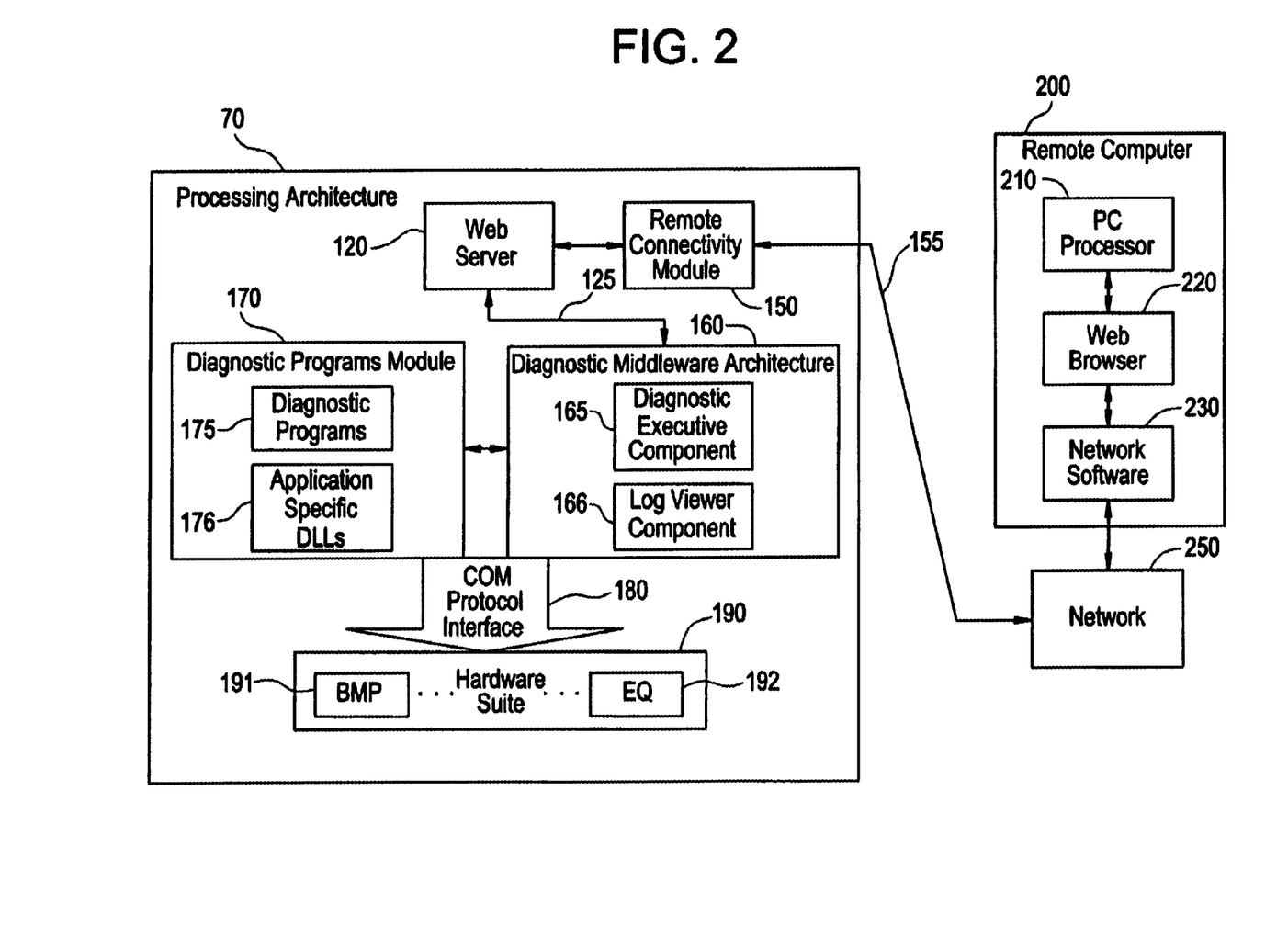
FIG. 2 is a schematic block diagram of a diagnostic configuration for the ultrasound scanner of FIG. 1, formed in accordance with an embodiment of the present invention, for generating diagnostic related information within the scanner and displaying the information at a remote location from the scanner.

FIG. 2 is a schematic block diagram of a diagnostic configuration for an ultrasound scanner 5 used for generating diagnostic information within the scanner 5 and displaying the diagnostic information at a remote location from the scanner 5 in accordance with an embodiment of the present invention. The higher level elements of the diagnostic configuration illustrated comprise processing architecture 70, a network 250, and a remote computer 200.

FIG. 2 shows the diagnostic-related aspects of the processing architecture 70 comprising a Java-based diagnostic middleware architecture 160, a diagnostic programs module 170, a hardware suite 190, a web server 120, and a remote connectivity module 150.

Within the processing architecture 70, web server 120 connects to remote connectivity module 150 and diagnostic middleware architecture 160, diagnostic middleware architecture 160 connects to diagnostic programs module 170. Hardware suite 190 interfaces to diagnostic middleware architecture 160 and diagnostic programs module 170 through a distributed object standard protocol interface 180, which may be a common object module (COM) interface.

Remote computer 200 comprises PC processor 210, web browser 220, network software 230, a keyboard and mouse (not shown), and a monitor (not shown). Network 250 interfaces remote computer 200 to processing architecture 70 in ultrasound scanner 5.

The diagnostic programs module 170 comprises various diagnostic programs 175 running on a computer and application specific dynamic link libraries (DLLs) which are custom to the platform. The Java-based diagnostic middleware architecture 160 comprises sets of Java servlets running on a computer and a Java native interface to C which are platform/server-independent. A java servlet is a java application that runs in a server-based system and provides server-side processing, typically to access information or initiate processing. The Java servlets are configured in a diagnostic executive component 165 and log viewer component 166. Java servlets and native interface to C are supported on most platforms including unix based platforms and windows based platforms.

The web server 120 comprises a computer running standard server software so as to establish a standard HyperText Transport Protocol (HTTP) server within the scanner 5 that is able to connect to the Internet. The web server 120 also comprises a set of HTML menus and Java applets to facilitate communication with remote computer 200. A java applet is a Java program that is downloaded from the server and run from the web browser. Java servlets and applets are more flexible than CGI scripts and are portable between platforms, servers, and operating systems.

In general, a web server provides WWW services on the Internet. A web server includes the hardware, operating system, web server software, TCP/IP protocols and web site content. The web server software refers to the HTTP server that manages web page requests from a browser and delivers HyperText Markup Language (HTML) documents (web pages) in response. The server also executes server-side scripts that provide functions such as data base searching.

HTTP is the communications protocol used to connect to web servers on the WWW. The primary function of HTTP is to establish a connection with a web server and transmit HTML pages to the client web browser.

The network 250 comprises the physical interface and software between the ultrasound scanner 5 and the remote computer 200. The network 250 may include telephone lines, routers and switchers, fiber optic cable, radio transmitters and receivers, or any other devices and software that may be used to establish a communications link between the ultrasound system 5 and remote computer 200. Typically, the network 250 comprises the Internet and the WWW. The web browser 220 is a program that serves as a front-end to the WWW on the Internet. The web browser 220 allows a user to view a site on the WWW.

The various architectures, suites, modules, and interfaces within the scanner may be combined or separated according to various embodiments of the present invention. For example, the processing architecture 70 may comprise dedicated hardware elements such as circuit boards with digital signal processors or may be software running on a general purpose computer or processor such as a commercial, off-the shelf PC. The diagnostic middleware architecture 160 and diagnostic programs module 170 may comprise software running on multiple dedicated computers or processors, or software running on a general purpose computer or processor such as a commercial, off-the-shelf PC.

The network 250 provides the communication link between the web server 120 within the scanner 5 and the remote computer 200. Within the remote computer 200, a PC processor 210 employs a web browser module 220 and a network software module 230. The PC processor 210 also interfaces to a keyboard (not shown), mouse (not shown), and monitor (not shown). The remote computer 200 executes software internal to the remote computer 200 in response to user inputs from a keyboard and mouse, and displays scanner diagnostic and status information on the monitor of the remote computer 200.

A system physically connects to a network through a port. An ultrasound scanner 5 may connect to a network 250 through, for example, a serial port. A modem is a device that converts information between the digital signals of a computer and the analog signals of telephone lines and vice-versa. Information from the web server 120 passes through the serial port on the digital side of the modem (i.e. between the server and modem). Communication with the modem is established by employing software that is known as a point-to-point (PPP) protocol. The PPP protocol is a standard protocol that allows multiple network protocols to be used over a serial connection such as a modem line. A network port and related functionality are provided by remote connectivity module 150.

Information is formatted and transferred across a network using software controlled communications protocols such as TCP/IP (Transmission Control Protocol/Internet Protocol). The IP protocol controls the routing of information through the network and the TCP protocol controls the actual transfer of information (packets) over the network.

An ultrasound scanner 5 may connect to a local network through, for example, an Ethernet connection. An Ethernet connection links the scanner to other scanners and systems on the local network. In a local Ethernet network, the systems on the network are within a certain allowable distance of each other and are connected through the same physical interface such as network wiring or fiber optic cable.

When information is to be sent from the ultrasound scanner 5 to a remote computer 200, the web server 120 employs the TCP/IP protocols to encapsulate the information into TCP packets. The TCP packets have header information that is used to track, check, and order the packets in the correct sequence for transmission. A given block of data comprises many packets and the packets may be routed differently over the Internet through different gateways. A gateway is a specialized computer used to connect and route packets of information between networks. The TCP protocol assures that the TCP packets are delivered to the correct destination in the correct order and without error.

Before transmission, the IP protocol is employed by the web server 120 to form IP packets from the TCP packets and having IP headers that provide addressing information that is used by the gateways to properly route the packets to their receiving destination. An IP header includes the Internet addresses of the source and destination. The IP protocol makes a best attempt to deliver all the packets but does not guarantee delivery.

At the receiving destination, (e.g. remote computer 200) the TCP packets are checked for errors according to the header information. Packets that are free of errors are acknowledged by the receiving destination and are placed in correct order to be reassembled into the original block of data. The transmitting source keeps track of packet acknowledgements. If a packet is not acknowledged in a certain amount of time, the packet is resent by the source (e.g. scanner 5). The receiving destination holds all received packets until all packets that make up the data block have been acknowledged. The packets are then correctly ordered and reassembled at the receiving destination.

TCP/IP is configured for the ultrasound scanner and the network environment to which the scanner is connected. For example, typical configuration information that is provided for TCP/IP comprises the user name and password associated with the scanner, the server address of the scanner, the IP address of the scanner, the type of local network the scanner may be connected to, and addresses of other scanners on the local network.

Every system connected to the Internet has a unique address. An IP address is a 32-bit address comprising four groups of 8 bits each separated by periods and specifying a connection to the Internet. A local network may use sub-network addressing such that each scanner on the local network has a sub-network address. The local network may be connected to the Internet as a single connection with a single IP address.

Domain name addressing is another type of addressing used in conjunction with the Internet where the user has a name associated with his network connection and the associated IP address number does not have to be directly known by the user. Domain name addressing is more convenient for the user since a meaningful domain name is preferable to a number.

The web server 120 in the scanner 5 is an HTTP server that interacts with the protocols (TCP/IP). The web server 120 is configured to communicate with a standard web browser 220 of a remote computer 200. The web browser 220 provides client requests to the web server 120 in order to initiate diagnostic programs 175 and access diagnostic information from the ultrasound scanner 5. The web server 120 responds to the client requests by providing web pages of information and hypertext connections that are displayed to the user on the remote computer 200. The web server 120 also interfaces with the Java-based diagnostic middleware architecture 160 to initiate diagnostic programs 175 in the diagnostic programs module 170 based on client requests from the remote computer 200, and also to gather diagnostic and status information from the scanner 5 stored in files.

The web server 120 is configured for such things as security by, for example, limiting access to certain users. Configuration information is stored in configuration files of the web server 120. Configuration files of the web server 120 may identify ports used by the web server 120 and, for example, the server administrator. The location of files used by the web server 120 are also included in the configuration files. The configuration files may also include the addresses of web pages and Java applets and servlets used by the web server 120.

In response to client requests by, for example, remote computer 200, the web server 120 transmits HyperText Markup Language (HTML) pages to the web browser 220. The HTML pages encapsulate what the web browser 220 may display on the monitor of remote computer 200. The displayed information may include text, images, buttons, etc. HTML pages are easily created using standard software tools. The HTML pages are stored on the scanner 5 and the addresses of the HTML pages are configured in the web server 120. When a remote computer (e.g. 200) requests to view a specific diagnostic web page of the scanner 5, the web server 120 finds the page and transmits its contents to the remote computer 200 over the network 250. The PC processor 210 executes the web browser module 220 to access the Internet through TCP/IP and PPP protocols configured for the remote computer 200. The remote computer 200 typically connects to the network 250 through a serial port and a modem in a similar manner as the scanner 5. The remote computer 200 used to access the scanner 5 is readily available commercially. Special hardware and software are not required.

The diagnostic middleware architecture 160 includes a set of small executable programs called Java servlets that provide an interface between the web server 120 and the diagnostic programs module 170. Diagnostic executive component 165 comprises a set of Java servlets to initiate execution of diagnostic programs 175 related to performing diagnostic tests on hardware suite 190. Log viewer component 166 comprises a set of Java servlets to initiate execution of diagnostic programs 175 related to performing productivity functions and retrieving diagnostic information from files.

In an embodiment of the present invention, the diagnostic middleware architecuture 160 commands the diagnostic programs module 170 to run a certain diagnostic program and provide requested diagnostic information such as diagnostic test data, productivity data, or ultrasound status data. In an embodiment of the present invention, the diagnostic middleware component 160 responds to client requests by dynamically generating custom HTML pages containing the requested information.

When a user clicks on a hypertext button (e.g. Initiate Scanner Diagnostics) on the monitor of the remote computer 200, a client request is transmitted over the network 250 to the web server 120 in the scanner 5. The web server 120 transfers the client request to the diagnostic middleware architecture 160 and the diagnostic middleware architecture 160 responds to the client request by initiating a diagnostic program within the diagnostic programs module 170 of the scanner 5. The diagnostic programs module 170 runs the diagnostics program and generates diagnostic data. The diagnostic middleware architecture interprets and translates the diagnostic data into an XML-based HTML page and the web server 120 transfers the HTML page over the network 250 to the remote computer 200 where the HTML page is displayed to the user on a monitor. Again, the diagnostic middleware architecture is platform/server independent and may be used on successive generations of ultrasound scanners and upgrades. CGI scripts, on the other hand, are specific to the platform and server and are not very portable to other platforms and operating systems.

As a specific example, a user may want to test a certain segment of memory in the range of addresses 0×1000 to 0×2000 in a B-mode processing (BMP) board 191 in hardware suite 190. The user applies the appropriate menus and java applets to establish a request on remote computer 200. The request is sent over the Internet to scanner 5 and is interpreted by diagnostic executive component 165 which then passes the correct command to execute the memory test on the BMP board 191 with the requested range of memory to be tested. The memory test is executed by interfacing with the BMP 191 through COM protocol interface 180. The results of the test are interpreted and translated to XML-based HTML format by the diagnostic executive component 165 and passed over the Internet by web server 120 using HTTP protocol to remote computer 200. The results are displayed on the monitor of remote computer 200 to the user. The results may include the status of the test, values passed from the BMP board 191, and other diagnostic program results.

The log viewer component 166 interprets various log files stored on the ultrasound scanner and presents a productive analysis to the user in response to client requests. The log viewer component 166 translates log files from a text format to a XML-based HTML page. The HTML page is transferred to the web browser 220 in remote computer 200 and is displayed per the style sheet defined for each log file. The method enables the various log files to have different presentations based on the information content. The log viewer component 166 also provides productivity-based functions including searching, analysis, and filtering which helps the user to understand the present functioning of the scanner. For example, a user trying to diagnose a problem with a scanner may filter the system log file to locate the errors and fix the errors.

The remote computer 200 is able to communicate with multiple ultrasound scanners over the Internet where the multiple scanners are based on different platform architectures and have different diagnostic programs modules, but employ the same type of common diagnostic middleware architecture as described above which is platform/server-independent.

In summary, the advantages and features include, among others, the ability to access ultrasound scanner information over the Internet from a remote location by employing a Java-based programs module within the scanner that is independent of the platform and server being used.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. Apparatus for diagnosing, from a third location, ultrasound scanners being at locations remote to said third location, said apparatus comprising:

a first ultrasound scanner being at a first location and being of a first platform type;

a second ultrasound scanner being at a second location, and being of a second platform type;

a first instance of a diagnostic middleware component initiating execution of a first diagnostic program for diagnosing said first ultrasound scanner at said first location to generate first diagnostic data of a first type in response to a first request originating from said third location, and translating said first diagnostic data to an Internet-compatible format at said first location;

a second instance of said diagnostic middleware component initiating a second diagnostic program for diagnosing said second ultrasound scanner at said second location to generate second diagnostic data of a second type in response to a second request originating from said third location, and translating said second diagnostic data to said Internet-compatible format at said second location;

a first instance of a web server cooperating with said first instance of said diagnostic middleware component at said first location to receive said first request at said first location, and to transfer said first diagnostic data in said Internet-compatible format from said first location to said third location through an Internet protocol-based interface; and a second instance of said web server cooperating with said second instance of said diagnostic middleware component at said second location to receive said request at said second location, and to transfer said second diagnostic data in said Internet-compatible format from said second location to said third location through said Internet protocol-based interface.

2. The apparatus of claim 1 wherein said first instance and said second instance of said diagnostic middleware component are configured to initiate a plurality of diagnostic programs at said first location and said second location.

3. The apparatus of claim 1 wherein said first instance and said second instance of said diagnostic middleware component comprise a common set of Java servlets and a common Java native interface to C.

4. The apparatus of claim 1 wherein said Internet-compatible format comprises XML-based HTML page format.

5. The apparatus of claim 1 further comprising a network interfacing said first location and said second location to said third location wherein said network comprises the Internet.

6. The apparatus of claim 1 further comprising a remote computer at said third location and a network external to said first ultrasound scanner and said second ultrasound scanner and said remote computer, said remote computer having a web browser and communicating with said first ultrasound scanner and said second ultrasound scanner through said network.

7. The apparatus of claim 1 further comprising a first hardware suite of said first ultrasound scanner interfacing to said first diagnostic program and said first instance of said diagnostic middleware component through a distributed object standard protocol interface, wherein said first diagnostic program is a first diagnostic hardware test and said diagnostic middleware component is a diagnostic executive component.

8. The apparatus of claim 1 further comprising a second hardware suite of said second ultrasound scanner interfacing to said second diagnostic program and said second instance of said diagnostic middleware component through a distributed object standard protocol interface, wherein said second diagnostic program is a second diagnostic hardware test and said diagnostic middleware component is a diagnostic executive component.

9. The apparatus of claim 1 wherein said diagnostic middleware component comprises a log viewer component and wherein said first diagnostic program comprises a first productivity function comprising one of searching for scanner information, analyzing scanner information, and filtering scanner information.

10. The apparatus of claim 1 wherein said diagnostic middleware component comprises a log viewer component and wherein said second diagnostic program comprises a second productivity function comprising one of searching for scanner information, analyzing scanner information, and filtering scanner information.

11. The apparatus of claim 1 wherein said diagnostic middleware component comprises a log viewer component and said first diagnostic program comprises a first file retrieving function to access and translate information in a first set of files stored at said first location for scanner diagnosing purposes.

12. The apparatus of claim 1 wherein said diagnostic middleware component comprises a log viewer component and said second diagnostic program comprises a second file retrieving function to access and translate information in a second set of files stored at said second location for scanner diagnosing purposes.

13. The apparatus of claim 1 further comprising a first instance of a remote connectivity module being at said first location and a network being external to said first ultrasound scanner, said first instance of said remote connectivity module interfacing said first instance of said web server to said network, and said first instance of said first remote connectivity module being based on Web technology.

14. The apparatus of claim 1 further comprising a second instance of a remote connectivity module being at said second location and a network being external to said second ultrasound scanner, said second instance of said remote connectivity module interfacing said second instance of said web server to said network, and said second instance of said second remote connectivity module being based on Web technology.

15. A method for diagnosing, from a third location, ultrasound scanners being at locations that are remote from said third location, said method comprising:

accessing a first instance of a web server at a first location from said third location by transferring a first instance of a menu and a first instance of user-interface programs from said first location to said third location in response to a first user input at said third location;

generating a first request at said third location by applying said first instance of said menu and said first instance of said user-interface programs at said third location;

transferring said first request to said first location and interpreting said first request at said first location resulting in executing a first diagnostic program at said first location, and said executing resulting in generating first diagnostic data of a first type for a first ultrasound scanner in response to said first request, and wherein said first ultrasound scanner is of a first platform type;

translating said first diagnostic data at said first location to an Internet-compatible format;

transferring said first diagnostic data in said Internet-compatible format from said first location to said third location for display at said third location;

accessing a second instance of a web server at a second location from said third location by transferring a second instance of said menu and a second instance of said user-interface programs from said second location to said third location in response to a second user input at said third location;

generating a second request at said third location by applying said second instance of said menu and said second instance of said user-interface programs at said third location;

transferring said second request to said second location and interpreting said second request at said second location resulting in executing a second diagnostic program at said second location, and said executing resulting in generating second diagnostic data of a second type for a second ultrasound scanner in response to said second request, and wherein said second ultrasound scanner is of a second platform type;

translating said second diagnostic data at said second location to an Internet-compatible format; and transferring said second diagnostic data in said Internet-compatible format from said second location to said third location for display at said third location.

16. The method of claim 15 further comprising generating a plurality of requests at said third location to initiate execution of a plurality of diagnostic programs at said first location and said second location.

17. The method of claim 15 wherein said menu is an XML-based HTML page.

18. The method of claim 15 wherein said user-interface programs are Java applets.

19. The method of claim 15 wherein said interpreting and translating is performed by employing platform/server-independent, Java-based programs at said first location and said second location, said Java-based programs comprising Java servlets and a Java native interface to C.

20. The method of claim 15 wherein said Internet-compatible format comprises an XML-based HTML page format.

21. The method of claim 15 wherein said first diagnostic program comprises a first diagnostic hardware test operating on a first hardware element of said first ultrasound scanner.

22. The method of claim 15 wherein said second diagnostic program comprises a second diagnostic hardware test operating on a second hardware element of said second ultrasound scanner.

23. The method of claim 15 wherein said first diagnostic program comprises a first productivity function comprising one of searching for scanner information, analyzing scanner information, and filtering scanner information.

24. The method of claim 15 wherein said second diagnostic program comprises a second productivity function comprising one of searching for scanner information, analyzing scanner information, and filtering scanner information.

25. The method of claim 15 wherein said first diagnostic program comprises a first file retrieving function to access and translate information in files stored at said first location.

26. The method of claim 15 wherein said second diagnostic program comprises a second file retrieving function to access and translate information in files stored at said second location.

27. The method of claim 15 wherein said first diagnostic data comprises information extracted from files of said first ultrasound scanner and said second diagnostic data comprises information extracted from files of said second ultrasound scanner, said information comprising scanner power information, scanner temperature information, scanner software functioning information, and scanner productivity information.

28. A diagnostic ultrasound scanner comprising:
a web server;
a Java-based diagnostics middleware component interfacing to said web server through an HTTP protocol interface;
a diagnostic programs module interfacing to said diagnostics middleware component; and
a hardware suite interfacing to said diagnostics middleware component and said diagnostic programs module through a COM protocol interface.

29. The ultrasound scanner of claim 28 further comprising a PC backend and a front-end, said PC backend interfacing to said front-end.

30. The ultrasound scanner of claim 28 further comprising a PC backend, said PC backend comprising an imaging mode processing module, a scan conversion module, a control processing module, and a display processing module.

31. The ultrasound scanner of claim 28 further comprising a remote connectivity module interfacing said web server to a network external to said ultrasound scanner.

32. The ultrasound scanner of claim 28 further comprising a monitor.

33. The ultrasound scanner of claim 28 wherein a remote computer, being at a location remote to said scanner, interfaces to said scanner through an Internet protocol-based network, said remote computer comprising a PC processor, a web browser, network software, and a network connection.

34. The ultrasound scanner of claim 28 wherein a remote computer, connecting to said scanner through an Internet protocol-based network, displays results of requested diagnostic tests, results of scanner productivity tests, scanner file information, and scanner status information to a user of said remote computer on a monitor of said remote computer at a location remote from said scanner.

35. Apparatus for diagnosing, from a third location, ultrasound scanners being at locations remote to said third location, said apparatus comprising:
a first ultrasound scanner being at a first location and being of a first platform type;
a second ultrasound scanner being at a second location, and being of a second platform type;
a first instance of a diagnostic middleware component, comprising a common set of Java servlets and a common Java native interface to C, initiating execution of a first diagnostic program for diagnosing said first ultrasound scanner at said first location to generate first diagnostic data of a first type in response to a first request originating from said third location, and translating said first diagnostic data to an Internet-compatible format at said first location;
a second instance of said diagnostic middleware component, comprising a common set of Java servlets and a common Java native interface to C, initiating a second diagnostic program for diagnosing said second ultrasound scanner at said second location to generate second diagnostic data of a second type in response to a second request originating from said third location, and translating said second diagnostic data to said Internet-compatible format at said second location;
a first instance of a web server cooperating with said first instance of said diagnostic middleware component at said first location to receive said first request at said first location, and to transfer said first diagnostic data in said Internet-compatible format from said first location to said third location through an Internet protocol-based interface; and
a second instance of said web server cooperating with said second instance of said diagnostic middleware component at said second location to receive said request at said second location, and to transfer said second diagnostic data in said Internet-compatible format from said second location to said third location through said Internet protocol-based interface.

36. The apparatus of claim 35 wherein said first instance and said second instance of said diagnostic middleware component are configured to initiate a plurality of diagnostic programs at said first location and said second location.

37. The apparatus of claim 35 wherein said Internet-compatible format comprises XML-based HTML page format.

38. The apparatus of claim 35 further comprising a network interfacing said first location and said second location to said third location wherein said network comprises the Internet.

39. The apparatus of claim 35 further comprising a remote computer at said third location and a network external to said first ultrasound scanner and said second ultrasound scanner and said remote computer, said remote computer having a web browser and communicating with said first ultrasound scanner and said second ultrasound scanner through said network.

40. The apparatus of claim 35 further comprising a first hardware suite of said first ultrasound scanner interfacing to said first diagnostic program and said first instance of said diagnostic middleware component through a distributed object standard protocol interface, wherein said first diagnostic program is a first diagnostic hardware test and said diagnostic middleware component is a diagnostic executive component.

41. The apparatus of claim 35 further comprising a second hardware suite of said second ultrasound scanner interfacing to said second diagnostic program and said second instance of said diagnostic middleware component through a distributed object standard protocol interface, wherein said second diagnostic program is a second diagnostic hardware test and said diagnostic middleware component is a diagnostic executive component.

42. The apparatus of claim 35 wherein said diagnostic middleware component comprises a log viewer component and wherein said first diagnostic program comprises a first productivity function comprising one of searching for scanner information, analyzing scanner information, and filtering scanner information.

43. The apparatus of claim 35 wherein said diagnostic middleware component comprises a log viewer component and wherein said second diagnostic program comprises a second productivity function comprising one of searching for scanner information, analyzing scanner information, and filtering scanner information.

44. The apparatus of claim 35 wherein said diagnostic middleware component comprises a log viewer component and said first diagnostic program comprises a first file retrieving function to access and translate information in a first set of files stored at said first location for scanner diagnosing purposes.

45. The apparatus of claim 35 wherein said diagnostic middleware component comprises a log viewer component and said second diagnostic program comprises a second file retrieving function to access and translate information in a second set of files stored at said second location for scanner diagnosing purposes.

46. The apparatus of claim 35 further comprising a first instance of a remote connectivity module being at said first location and a network being external to said first ultrasound scanner, said first instance of said remote connectivity module interfacing said first instance of said web server to said network, and said first instance of said first remote connectivity module being based on Web technology.

47. The apparatus of claim 35 further comprising a second instance of a remote connectivity module being at said second location and a network being external to said second ultrasound scanner, said second instance of said remote connectivity module interfacing said second instance of said web server to said network, and said second instance of said second remote connectivity module being based on Web technology.

48. Apparatus for diagnosing, from a third location, ultrasound scanners being at locations remote to said third location, said apparatus comprising:

a first ultrasound scanner being at a first location and being of a first platform type;

a second ultrasound scanner being at a second location, and being of a second platform type;

a first instance of a diagnostic middleware component initiating execution of a first diagnostic program for diagnosing said first ultrasound scanner at said first location to generate first diagnostic data of a first type in response to a first request originating from said third location, and translating said first diagnostic data to an Internet-compatible format at said first location;

a second instance of said diagnostic middleware component initiating a second diagnostic program for diagnosing said second ultrasound scanner at said second location to generate second diagnostic data of a second type in response to a second request originating from said third location, and translating said second diagnostic data to said Internet-compatible format at said second location;

a first instance of a web server cooperating with said first instance of said diagnostic middleware component at said first location to receive said first request at said first location, and to transfer said first diagnostic data in said Internet-compatible format from said first location to said third location through an Internet protocol-based interface;

a second instance of said web server cooperating with said second instance of said diagnostic middleware component at said second location to receive said request at said second location, and to transfer said second diagnostic data in said Internet-compatible format from said second location to said third location through said Internet protocol-based interface; and a first hardware suite of said first ultrasound scanner interfacing to said first diagnostic program and said first instance of said diagnostic middleware component through a distributed object standard protocol interface, wherein said first diagnostic program is a first diagnostic hardware test and said diagnostic middleware component is a diagnostic executive component.

49. Apparatus for diagnosing, from a third location, ultrasound scanners being at locations remote to said third location, said apparatus comprising:

a first ultrasound scanner being at a first location and being of a first platform type;

a second ultrasound scanner being at a second location, and being of a second platform type;

a first instance of a diagnostic middleware component initiating execution of a first diagnostic program for diagnosing said first ultrasound scanner at said first location to generate first diagnostic data of a first type in response to a first request originating from said third location, and translating said first diagnostic data to an Internet-compatible format at said first location;

a second instance of said diagnostic middleware component initiating a second diagnostic program for diagnosing said second ultrasound scanner at said second location to generate second diagnostic data of a second type in response to a second request originating from said third location, and translating said second diagnostic data to said Internet-compatible format at said second location;

a first instance of a web server cooperating with said first instance of said diagnostic middleware component at said first location to receive said first request at said first location, and to transfer said first diagnostic data in said Internet-compatible format from said first location to said third location through an Internet protocol-based interface;

a second instance of said web server cooperating with said second instance of said diagnostic middleware component at said second location to receive said request at said second location, and to transfer said second diagnostic data in said Internet-compatible format from said second location to said third location through said Internet protocol-based interface; and a second hardware suite of said second ultrasound scanner interfacing to said second diagnostic program and said second instance of said diagnostic middleware component through a distributed object standard protocol interface, wherein said second diagnostic program is a second diagnostic hardware test and said diagnostic middleware component is a diagnostic executive component.

50. A method for diagnosing, from a third location, ultrasound scanners being at locations that are remote from said third location, said method comprising:

accessing a first instance of a web server at a first location from said third location by transferring a first instance of a menu and a first instance of user-interface programs from said first location to said third location in response to a first user input at said third location;

generating a first request at said third location by applying said first instance of said menu and said first instance of said user-interface programs at said third location;

transferring said first request to said first location and interpreting said first request at said first location resulting in executing a first diagnostic program at said first location, and said executing resulting in generating first diagnostic data of a first type for a first ultrasound scanner in response to said first request, wherein said interpreting comprises employing platform/server-independent, Java-based programs at said first location, said Java-based programs comprising Java servlets and a Java native interface to C;

translating said first diagnostic data at said first location to an Internet-compatible format, wherein said translating comprises employing platform/server-independent, Java-based programs at said first location, said Java-based programs comprising Java servlets and a Java native interface to C;

transferring said first diagnostic data in said Internet-compatible format from said first location to said third location for display at said third location;

accessing a second instance of a web server at a second location from said third location by transferring a second instance of said menu and a second instance of said user-interface programs from said second location to said third location in response to a second user input at said third location;

generating a second request at said third location by applying said second instance of said menu and said second instance of said user-interface programs at said third location;

transferring said second request to said second location and interpreting said second request at said second location resulting in executing a second diagnostic program at said second location, and said executing resulting in generating second diagnostic data of a second type for a second ultrasound scanner in response to said second request, wherein said interpreting comprises employing platform/server-independent, Java-based programs at said second location, said Java-based programs comprising Java servlets and a Java native interface to C;

translating said second diagnostic data at said second location to an Internet-compatible format, wherein said translating comprises employing platform/server-independent, Java-based programs at said second location, said Java-based programs comprising Java servlets and a Java native interface to C; and transferring said second diagnostic data in said Internet-compatible format from said second location to said third location for display at said third location.

51. The method of claim 50 further comprising generating a plurality of requests at said third location to initiate execution of a plurality of diagnostic programs at said first location and said second location.

52. The method of claim 50 wherein said menu is an XML-based HTML page.

53. The method of claim 50 wherein said user-interface programs are Java applets.

54. The method of claim 50 wherein said Internet-compatible format comprises an XML-based HTML page format.

55. The method of claim 50 wherein said first diagnostic program comprises a first diagnostic hardware test operating on a first hardware element of said first ultrasound scanner.

56. The method of claim 50 wherein said second diagnostic program comprises a second diagnostic hardware test operating on a second hardware element of said second ultrasound scanner.

57. The method of claim 50 wherein said first diagnostic program comprises a first productivity function comprising one of searching for scanner information, analyzing scanner information, and filtering scanner information.

58. The method of claim 50 wherein said second diagnostic program comprises a second productivity function comprising one of searching for scanner information, analyzing scanner information, and filtering scanner information.

59. The method of claim 50 wherein said first diagnostic program comprises a first file retrieving function to access and translate information in files stored at said first location.

60. The method of claim 50 wherein said second diagnostic program comprises a second file retrieving function to access and translate information in files stored at said second location.

61. The method of claim 50 wherein said first diagnostic data comprises information extracted from files of said first ultrasound scanner and said second diagnostic data comprises information extracted from files of said second ultrasound scanner, said information comprising scanner power information, scanner temperature information, scanner software functioning information, and scanner productivity information.

62. A method for diagnosing, from a third location, ultrasound scanners being at locations that are remote from said third location, said method comprising:

accessing a first instance of a web server at a first location from said third location by transferring a first instance of a menu and a first instance of user-interface programs from said first location to said third location in response to a first user input at said third location;

generating a first request at said third location by applying said first instance of said menu and said first instance of said user-interface programs at said third location;

transferring said first request to said first location and interpreting said first request at said first location resulting in executing a first diagnostic program at said first location, and said executing resulting in generating first diagnostic data of a first type for a first ultrasound scanner in response to said first request, wherein said first diagnostic data comprises information extracted from files of said first ultrasound scanner, and said information comprising scanner power information, scanner temperature information, scanner software functioning information, and scanner productivity information;

translating said first diagnostic data at said first location to an Internet-compatible format;

transferring said first diagnostic data in said Internet-compatible format from said first location to said third location for display at said third location;

accessing a second instance of a web server at a second location from said third location by transferring a second instance of said menu and a second instance of said user-interface programs from said second location to said third location in response to a second user input at said third location;

generating a second request at said third location by applying said second instance of said menu and said second instance of said user-interface programs at said third location;

transferring said second request to said second location and interpreting said second request at said second location resulting in executing a second diagnostic program at said second location, and said executing resulting in generating second diagnostic data of a second type for a second ultrasound scanner in response to said second request, wherein said second diagnostic data comprises information extracted from files of said second ultrasound scanner, and said information comprising scanner power information, scanner temperature information, scanner software functioning information, and scanner productivity information;

translating said second diagnostic data at said second location to an Internet-compatible format; and transferring said second diagnostic data in said Internet-compatible format from said second location to said third location for display at said third location.

* * * * *